United States Patent [19]

Cummins et al.

[11] Patent Number: 5,188,820
[45] Date of Patent: Feb. 23, 1993

[54] METHOD OF INHIBITING PLAQUE ON TEETH BY APPLYING AN ORAL COMPOSITION

[75] Inventors: Diane Cummins, West Kirby; Franciscus J. van der Ouderaa, Neston, both of England

[73] Assignee: Chesebrough-Pond's USA Co., Dividion of Conopco, Inc., Greenwich, Conn.

[21] Appl. No.: 769,142

[22] Filed: Sep. 27, 1991

Related U.S. Application Data

[63] Continuation of Ser. No. 592,421, Oct. 3, 1990, abandoned.

[30] Foreign Application Priority Data

Oct. 5, 1989 [GB] United Kingdom ............... 8922434

[51] Int. Cl.$^5$ ..................... A61K 7/16; A61K 7/18
[52] U.S. Cl. ........................ 424/49; 424/52; 424/57; 424/641
[58] Field of Search ..................... 424/49, 52

[56] References Cited

U.S. PATENT DOCUMENTS

| | | | |
|---|---|---|---|
| 3,989,814 | 11/1976 | Cordon | 424/57 |
| 4,022,880 | 5/1977 | Vinson et al. | 424/52 |
| 4,289,754 | 9/1981 | Dhabhar et al. | 424/52 |
| 4,430,324 | 2/1984 | Viccaro | 424/52 |
| 4,459,277 | 7/1984 | Kosti | 424/58 |
| 4,664,906 | 5/1987 | Sipos | 424/49 |
| 4,689,214 | 8/1987 | Niles | 424/49 |
| 4,719,100 | 1/1988 | Frosch | 424/49 |
| 4,894,220 | 1/1990 | Nabi | 424/57 |
| 4,927,625 | 5/1990 | Duckworth | 424/52 |
| 5,000,940 | 3/1991 | Staples | 424/49 |
| 5,004,597 | 4/1991 | Majeti | 424/49 |
| 5,057,308 | 10/1991 | Hill | 424/49 |
| 5,059,416 | 10/1991 | Cherwkuri | 424/49 |

FOREIGN PATENT DOCUMENTS

| | | |
|---|---|---|
| 523080 | 7/1979 | Australia . |
| 0074082 | 3/1983 | European Pat. Off. . |
| 0075446 | 3/1983 | European Pat. Off. . |
| 0297563 | 1/1989 | European Pat. Off. . |

OTHER PUBLICATIONS

"Tooth Surface Interactions and Preventive Dentistry" by Svatun and Rolla, pp. 33–37 (1981).

Primary Examiner—Thurman K. Page
Assistant Examiner—Raj Bawa
Attorney, Agent, or Firm—Milton L. Honig

[57] ABSTRACT

Oral compositions such as dentifrices with an improved anti-plaque efficacy are obtained by inclusion therein of a mixture of a stannous salt such as stannousfluoride or stannouspyrophosphate and a zinc salt such as zinc citrate.

3 Claims, No Drawings

METHOD OF INHIBITING PLAQUE ON TEETH BY APPLYING AN ORAL COMPOSITION

This is a continuation application of Ser. No. 07/592,421, filed Oct. 3, 1990, now abandoned.

The present invention relates to oral compositions such as dentifrices, mouthwashes, gels, subgingival rinse compositions, toothpastes, toothpowders, chewing gum, prophylactic pastes, lozenges, flosses, toothpicks which provide anti-plaque benefits.

In the prior art an abundancy of proposals has been made to obtain anti-plaque oral compositions. Many of these proposals have however not resulted in a reasonably effective anti-plaque oral composition. One of the few really effective anti-plaque oral compositions is based upon the use of a zinc compound as an anti-plaque agent. This is more fully described in e.g. U.S. Pat. No. 4,022,880 (Vinson et al). Another material which has been considered as anti-plaque agent is the stannous ion. This has e.g. been discussed in "Tooth Surface Interactions and Preventive Dentistry", IRL Press Ltd (London) 1981, pages 33-37, "The role of stannous pyrophosphate in the plaque-inhibiting effect of dentifrices containing stannous fluoride" by Svatun and Rolla. Despite the many disclosures in the anti-plaque area, the need for further improved anti-plaque products exists, which are properly balanced with regard to efficacy and undesired possible adverse reaction in the mouth.

It has now been found that a stannous compound when used in combination with a zinc compound provides an improved anti-plaque efficacy. Consequently, in its broadest aspect the present invention relates to an oral composition with an improved anti-plaque activity, comprising a mixture of a stannous compound and a zinc compound as the anti-plaque active system.

The stannous compound, suitable for use in the present invention, can be any stannous compound with inorganic or organic counter ions. It can be a highly soluble stannous salt, or it can be a sparingly soluble stannous salt. Highly soluble stannous salts are e.g. stannous fluoride, stannous chloride, stannous chloride fluoride, stannous acetate, sodium stannous fluoride, potassium stannous fluoride, stannous hexafluorozirconate, stannous sulfate, stannous tartrate, stannous gluconate, disodium mono-stannous citrate etc. Of these highly soluble stannous salts stannous fluoride is the preferred stannous salt.

Sparingly soluble stannous salts are e.g. stannous pyrophosphate, stannous metaphosphate, stannous oxalate stannous phosphate, distannous citrate etc. Stannous pyrophosphate is a preferred sparingly soluble stannous salt. Mixtures of various highly soluble stannous salts may also be used, as well as mixtures of various sparingly soluble stannous salts and mixtures of highly and sparingly soluble stannous salts. A preferred mixture is the mixture of stannous fluoride and stannous pyrophosphate.

Although highly soluble stannous salts can be used in the present invention, they tend to be not sufficiently stable upon storage. The stannous ions, dissolved in an aqueous solution tend to be converted therein to inert tin compounds, which do not provide for a reasonable anti-plaque activity. Therefore, if a highly soluble stannous salt is used, care should be taken to reduce the quantity of active dissolved stannous ions during storage of the oral composition, or to stabilize the stannous ions by other means.

When using a sparingly soluble stannous salt, care should be taken that there is a sufficient level of active dissolved stannous ions in the composition without giving rise to precipitation thereof as e.g. stannous oxide or stannous oxide hydrate. One way of achieving this is by solubilising the stannous salt, e.g. the stannous pyrophosphate with a certain amount of an alkalimetal pyrophosphate, or an alkalimetal citrate, or a fluoride source.

In general, the stannous salt is used in such an amount in the oral composition, that there is an effective amount of active dissolved stannous ions available in the composition to achieve an anti-plaque efficacy. For the highly soluble stannous salts this amount will generally range from 0.01-10%, preferably from 0.02-5 and particularly preferably from 0.1-3% by weight of the oral composition. As regards the sparingly soluble stannous salts these ranges are 0.05-10, preferably 0.1-5 and particularly 0.1-3% by weight of the oral composition.

The zinc compound, suitable for use in the present invention can be any highly soluble or sparingly soluble zinc compound having inorganic or organic counter ions. Suitable examples of such zinc salts are enumerated in U.S. Pat. No. 4,022,880 (Vinson et al), which is hereby incorporated by way of reference. A preferred zinc salt is zinc citrate trihydrate. In general, the amount of zinc salt used in the present invention ranges from 0.05-5% (calculated as zinc ion), preferably from 0.1-4% the oral composition.

The oral composition of the present invention may contain an orally acceptable medium which contains usual additional ingredients in conventional amounts, depending upon the final form of the composition, i.e. a dentifrice, a mouthwash, a gel and the like. Thus, as dentifrice it will usually comprise an abrasive cleaning agent in an amount of from 3-75% by weight. Suitable abrasive cleaning agents are milled or unmilled particulate aluminas; silica xerogels, hydrogels and aerogels and precipitated particulate silicas; calciumpyrophosphate; insoluble sodium metaphosphate; calcium carbonate; dicalcium orthophosphate; particulate hydroxyapatite and so on.

Furthermore, the dentifrice may contain a liquid phase comprising water and a humectant in an amount of 10-99% by weight. Typical humectants are glycerol, sorbitol, polyethyleneglycol, polypropylene glycol, propylene glycol, hydrogenated partially hydrolyzed polysaccharides and so on.

Binders or thickening agents such as sodium carboxymethylcellulose, hydroxyethylcellulose, hydroxypropylcellulose, xanthan gums, Irish moss, gum tragacanth, finely-divided silicas and hectorites may also be included in the dentifrice in an amount of 0.5-10% by weight. Another conventional ingredient in a dentifrice is an organic surfactant such as a soap, an anionic, nonionic, cationic, ampholytic and/or a zwitterionic synthetic detergent surfactant in an amount of 0.2-5% by weight.

When the composition is in the form of a mouthwash, it will usually contain an alcohol, a solubilizer, and when in the form of a gel it will usually contain a thickening agent.

Various other optional ingredients may be included in the compositions of the invention, such as flavouring agents, sweetening agents such as sodium saccharinate, whitening agents such as titanium dioxide or zinc oxide, preservatives, vitamins such as vitamin C and E, other anti-plaque agents such as copper salts, sanguinarine, allantoin, p-aminobenzoic acid derivates, hexetidine, chlorhexidine, 3-(4-propylheptyl)-4-(2-hydroxyethyl)-morpholine, anti-bacterial agents such as Triclosan (2′,4,4′-trichloro-2-hydroxy-diphenyl ether), anti-calculus agents such as di- and/or tetra-alkalimetalpyrophosphates, pH adjusting agents, colouring agents, anticaries agents such as casein, casein digests, sodium trimetaphosphate, sodium fluoride and monosodium-fluorophosphate, anti-staining compounds such as silicone polymers, anti-inflammatory agents such as substituted salicylanilides, plant extracts, desensitizing agents for sensitive teeth such as potassium nitrate and potassium citrate, polymers such as polyvinylmethylether-maleic anhydride copolymers and so on.

The compositions of the present invention not only provide for an improved anti-plaque efficacy, but also have an anti-gingivitis and an anti-calculus benefit. The mixture of the stannous salt and the zinc salt can also be used in the manufacture of a medicament against gingivitis. The mixture also has an improved anti-microbial effect on the oral flora. The stannous salt and zinc salt may be used in the same phase of the oral composition, or they may each be present in a separate phase, e.g. one of them may be present in the stripe phase of a so-called striped toothpaste and the other one may be present in the main phase of such a striped toothpaste. When a fluoride source is also present in the composition, this may also be present in the phase, separate from the stannous salt containing phase.

The oral compositions of the present invention can be formulated to any desirable pH-value. It is preferred that the compositions have a pH of between 3.5 and 5.5.

The present invention will now be further illustrated by the following Examples.

EXAMPLE 1

The effectiveness of the dentifrice compositions of this invention in inhibiting the growth of plaque on the teeth was determined by following a standard procedure for the measurement of plaque growth. The methodology of measuring plaque growth is that according to Harrap as described in J. Clin. Periodontol., 1974, 1, 166–174 which gives a procedure for assessing the amount of plaque on the teeth adjacent to the gingival margin. The procedure is as follows:

During the late afternoon each subject brushes his/her teeth with a simple, non-active paste (having a composition as given hereinafter) for an unspecified period of time to remove as much plaque as possible. This is immediately followed by brushing for one minute with 1.5 g of the allocated test paste. Residual paste is removed by rinsing the mouth with water and any remaining plaque disclosed by painting the teeth with an aqueous solution of Erythrosin (0.5% w/w) using a soft camel hair brush. Excess dye is removed by rinsing with water and the amount of plaque assessed and recorded for each of 16 teeth (numbers 3 to 6 for each quadrant). The recorded plaque is designated $P_0$.

No further oral hygiene is permitted for 18 hours after which time each subject rinses his/her mouth with water to remove food debris and viscous saliva. Plaque assessment is then carried out as before and recorded ($P_{18}$). The values of $P_{18}-P_0$ for each tooth are averaged to give a $P_{18}-P_0$ value per mouth. The mean of the values obtained for the subjects in the test is the plaque growth value. Panels of at least 12 subjects are used. The plaque growth value for a toothpaste without active ingredients is usually in the range 22 to 26. The plaque growth inhibition (PGI) is then computed for each test treatment by expressing the percentage inhibition compared to placebo:

$$PGI = \frac{PG_{pl} - PG_T}{PG_{pl}} \times 100\%$$

The composition of the simple, non-active toothpaste referred to above was the following:

| Ingredient | % |
| --- | --- |
| Alumina trihydrate | 50.00 |
| Glycerin | 27.00 |
| Hydroxyethylcellulose | 0.95 |
| Titanium dioxide | 0.50 |
| Water | to 100.00 |

The following compositions were assessed as to their PGI in accordance with the above test protocol.

| | Composition (in % by weight) | | | | | |
| --- | --- | --- | --- | --- | --- | --- |
| | A | B | C | D | E | F |
| Silica xerogel | 14.0 | 14.0 | 14.0 | 14.0 | 14.0 | 14.0 |
| Silica aerogel | 9.0 | 9.0 | 9.0 | 9.0 | 9.0 | 9.0 |
| Sorbitol syrup (70%) | 45.0 | 45.0 | 45.0 | 45.5 | 45.0 | 45.0 |
| Polyethyleneglycol (MW 1500) | 5.0 | 5.0 | 5.0 | 5.0 | 5.0 | 5.0 |
| Xanthan gum | 0.6 | 0.6 | 0.6 | 0.6 | 0.6 | 0.6 |
| Saccharin | 0.23 | 0.23 | 0.23 | 0.23 | 0.23 | 0.23 |
| Benzoic acid | 0.19 | 0.19 | 0.19 | 0.19 | 0.19 | 0.19 |
| Titanium dioxide | 1.0 | 1.0 | 1.0 | 1.0 | 1.0 | 1.0 |
| Sodium laurylsulphate | 1.5 | 1.5 | 1.5 | 1.5 | 1.5 | 1.5 |
| Flavour | 1.0 | 1.0 | 1.0 | 1.0 | 1.0 | 1.0 |
| Sodium fluoride | — | — | — | 0.33 | — | 0.33 |
| Monosodium fluorophosphate | 1.1 | 1.1 | 1.1 | — | 1.1 | — |
| Stannouspyrophosphate | 1.0 | 2.0 | — | 1.0 | 1.0 | 1.0 |
| Zinc citrate trihydrate | — | — | 0.5 | — | 0.5 | 0.5 |
| Water | to 100 | to 100 | to 100 | to 100 | to 100 | to 100 |
| PGI-values | 26 | 16 | 14/9 | 0 | — | — |
| | 25 | — | — | — | 32 | 34 |
| | 24 | — | 30 | — | 50;37;41 | — |
| | 26 | — | — | 0 | 42;38 | — |

EXAMPLE 2

The following formulations were tested as to their plaque growth inhibition effect in the manner as described in Example 1.

| | Composition (% by weight) | | |
| --- | --- | --- | --- |
| | G | H | J |
| Alumina | 54.25 | 54.75 | 55.25 |
| Sorbitol (70%) | 27 | 27 | 27 |
| Xanthan gum | 0.88 | 0.88 | 0.88 |
| Titanium dioxide | 0.5 | 0.5 | 0.5 |
| Sodium laurylsulphate | 1.5 | 1.5 | 1.5 |
| Saccharin | 0.23 | 0.23 | 0.23 |
| Benzoic acid | 0.19 | 0.19 | 0.19 |
| Flavour | 1.0 | 1.0 | 1.0 |
| Stannous pyrophosphate | — | 1.0 | 1.0 |
| Monosodium fluorophosphate | 1.1 | 1.1 | 1.1 |
| Zinc citrate trihydrate | — | — | 0.5 |
| Water | to 100 | to 100 | to 100 |
| PGI value (mean) | 0 | 23 | 33 |

Again the anti-plaque efficacy of the composition of the invention (J) was superior to that of the comparative formulations (G,H).

Example 3

The following formulations were made, and their PGI values determined in the manner as described in Example 1.

|  | Composition (% by weight) | |
| --- | --- | --- |
|  | K | L |
| Silica xerogel | 10.50 | 10.50 |
| Silica aerogel | 10.00 | 10.00 |
| Sorbitol (70%) | 67.87 | 67.95 |
| Polyethyleneglycol (MW 1500) | 5.0 | 5.0 |
| Ethanol | 1.8 | 1.8 |
| Sodium laurylsulphate | 1.47 | 1.47 |
| Flavour | 0.77 | 0.77 |
| Sodium carboxymethylcellulose | 0.3 | 0.3 |
| Sodium saccharin | 0.3 | 0.3 |
| Colouring agent | 0.15 | 0.15 |
| Sodium benzoate | 0.08 | 0.08 |
| Flavour enhancer | 0.4 | 0.4 |
| Sodium hydroxide (50% solution) | 0.25 | — |
| Stannous fluoride | 0.46 | — |
| Zinc citrate trihydrate | 0.50 | 0.50 |
| Stannous pyrophosphate | — | 1.00 |
| Sodium fluoride | — | 0.25 |
| Water | to 100 | to 100 |
| PGI-value (mean) | 30 | 32 |

EXAMPLE 4

The reduction in plaque and gingivitis of three formulations was investigated in two 21 days experimental gingivitis studies, in the manner as described by C. A. Saxton, "The effect of dentifrice containing zinc citrate and Triclosan in developing gingivitis", Journal of Periodontal Research 24 (1989) page 75. The formulations tested in study I were formulations E and C, and in study II formulation E was tested as well as the following formulation M.

|  | M (in % by weight) |
| --- | --- |
| Silica xerogel | 10.00 |
| Silica aerogel | 8.50 |
| Sorbitol (70%) | 45.00 |
| Polyethyleneglycol (MW 1500) | 5.00 |
| Sodium laurylsulphate | 1.5 |
| Titanium dioxide | 1.0 |
| Sodium carboxymethylcellulose | 0.9 |
| Saccharin | 0.2 |
| Flavour | 1.0 |
| Monosodium fluorophosphate | 0.80 |
| Zinc citrate trihydrate | 0.50 |
| Stannouspyrophosphate | 1.00 |
| Triclosan | 0.50 |
| Water | to 100. |

The results of the studies were as follows:

| Formulation | Plaque reduction | | Gingivitis reduction | |
| --- | --- | --- | --- | --- |
|  | Study I | Study II | Study I | Study II |
| C | 9% | — | 19% | — |
| E | 19% | 27% | 43% | 47% |
| M | — | 39% | — | 62% |

(— = not tested in the study)

These data show a clearly superior anti-plaque and anti-gingivitis efficacy of compositions according to the present invention.

EXAMPLE 5

The relative antiplaque activities of toothpaste formulations N, O and P were assessed using a 48-hour plaque screening model. Formulation N was similar to formulation K of Example 3, save that it did not contain zinc citrate; Formulation O was identical to Formulation K and Formulation P was similar to Formulation L of Example 3, save that it contained 0.46% stannous fluoride instead of 0.25% sodium fluoride. Studies were conducted in a double blind manner, with neither examiner nor panelists having knowledge of the product identity. Panelists were required to meet certain entrance criteria in order to be included in the study.

Panelists received a full mouth supragingival prophylaxis and scaling. Panelists were then instructed to refrain from all oral hygiene measures, except use of assigned test products, for the next 48 hours. Treatments were performed twice a day, in the morning (supervised) and in the evening, for two days. The following day the panelists used a disclosing solution and were then examined for plaque on the Ramford teeth using the DMPI (=Distal Mesial plaque index) plaque scoring system.

Treatments were prepared as follows: Panelists used 15 milliliters of a 25% toothpaste slurry for each treatment. Treatment slurries were prepared fresh daily.

The following results were obtained:

| Formulation | % plaque growth inhibition vs. placebo (water) |
| --- | --- |
| N | 24.3 |
| O | 40.6 |
| P | 55.6 |

We claim:
1. A method for inhibiting plaque on teeth comprising applying to said teeth an oral composition comprising:
   (i) from 0-75% by weight of the composition of an abrasive cleaning agent selected from the group consisting of milled particulate aluminas, unmilled particulate aluminas, silica xerogels, silica hydrogels, silica aerogels, precipitated particulate silicas, insoluble sodium metaphosphate, calcium carbonate, dicalcium orthophosphate, particulate hydroxyapatite, and mixtures thereof; and
   (ii) an anti-plaque active system comprising a mixture of:
      (a) 0.01-10% by weight, based on the total composition, of a stannous salt selected from the group consisting of stannous fluoride, stannous pyrophosphate, and mixtures thereof; and
      (b) 0.05-5% by weight, calculated as zinc ion, based on the total composition, of a zinc salt which is zinc citrate trihydrate.
2. A method according to claim 1 wherein the stannous salt is stannous pyrophosphate.
3. A method according to claim 1 wherein the stannous salt is a combination of from 0.1 to 5% by weight stannous pyrophosphate and from 0.02 to 5% by weight stannous fluoride.

* * * * *